United States Patent
Amery

[11] Patent Number: 5,961,502
[45] Date of Patent: Oct. 5, 1999

[54] SELF-SUPPORTING OSTOMY POUCH

[75] Inventor: Michael J. Amery, Washington Crossing, Pa.

[73] Assignee: Bristol-Myers Squibb Company, Princeton, N.J.

[21] Appl. No.: 08/810,098

[22] Filed: Mar. 3, 1997

Related U.S. Application Data

[63] Continuation of application No. 08/445,609, May 22, 1995, abandoned.

[51] Int. Cl.$^6$ .......................................................... A61F 5/44
[52] U.S. Cl. ............................ 604/332; 604/338; 604/339
[58] Field of Search ..................................... 604/332, 334, 604/336, 337, 338, 339, 344, 345; 600/29, 32; 383/4, 11; 206/803, 813; 229/74

[56] References Cited

U.S. PATENT DOCUMENTS

| | | | |
|---|---|---|---|
| 2,117,621 | 5/1938 | Mills | 604/337 |
| 3,202,193 | 8/1965 | Ware | 383/4 |
| 3,339,826 | 9/1967 | Beskind | 229/74 |
| 3,507,444 | 4/1970 | Werby | 229/74 |
| 3,525,470 | 8/1970 | Carrigan | 229/74 |
| 3,690,320 | 9/1972 | Ricky | 604/336 |
| 3,712,304 | 1/1973 | Marsan | 604/336 |
| 3,900,059 | 8/1975 | Kirk et al. | 383/11 |
| 3,941,133 | 3/1976 | Chen | 604/336 |
| 4,232,672 | 11/1980 | Steer et al. | 604/336 |
| 4,403,991 | 9/1983 | Hill | 604/338 |
| 4,411,659 | 10/1983 | Jensen et al. | 604/332 |
| 5,009,648 | 4/1991 | Aronoff et al. | 604/338 |
| 5,085,652 | 2/1992 | Johnsen et al. | 604/339 |
| 5,248,307 | 9/1993 | Sokoloff | 604/332 |
| 5,403,299 | 4/1995 | Schneider | 604/332 |

FOREIGN PATENT DOCUMENTS 3743003 4/1989 Germany.

OTHER PUBLICATIONS

Hollister Incorporation, Product Data Sheet: Ostomy, 1982.
Hollister Incorporated, Product Data Sheet: Ostomy, 901063–282.

*Primary Examiner*—John G. Weiss
*Assistant Examiner*—David J. Cho
*Attorney, Agent, or Firm*—Stuart E. Krieger

[57] ABSTRACT

The waste collection pouch has a wall adapted to be situated adjacent the body and a stoma receiving inlet. A collar may be affixed to the wall around the inlet and coated with an adhesive layer. An adhesive layer is provided directly on the pouch wall, either covering the entire surface of the wall or a section along the periphery, so as to affix the pouch wall directly to the body. The pouch may have an oval shape with its major axis adapted to extend laterally or may be circular. The bottom edge may be linear or include an inwardly indented section.

10 Claims, 6 Drawing Sheets

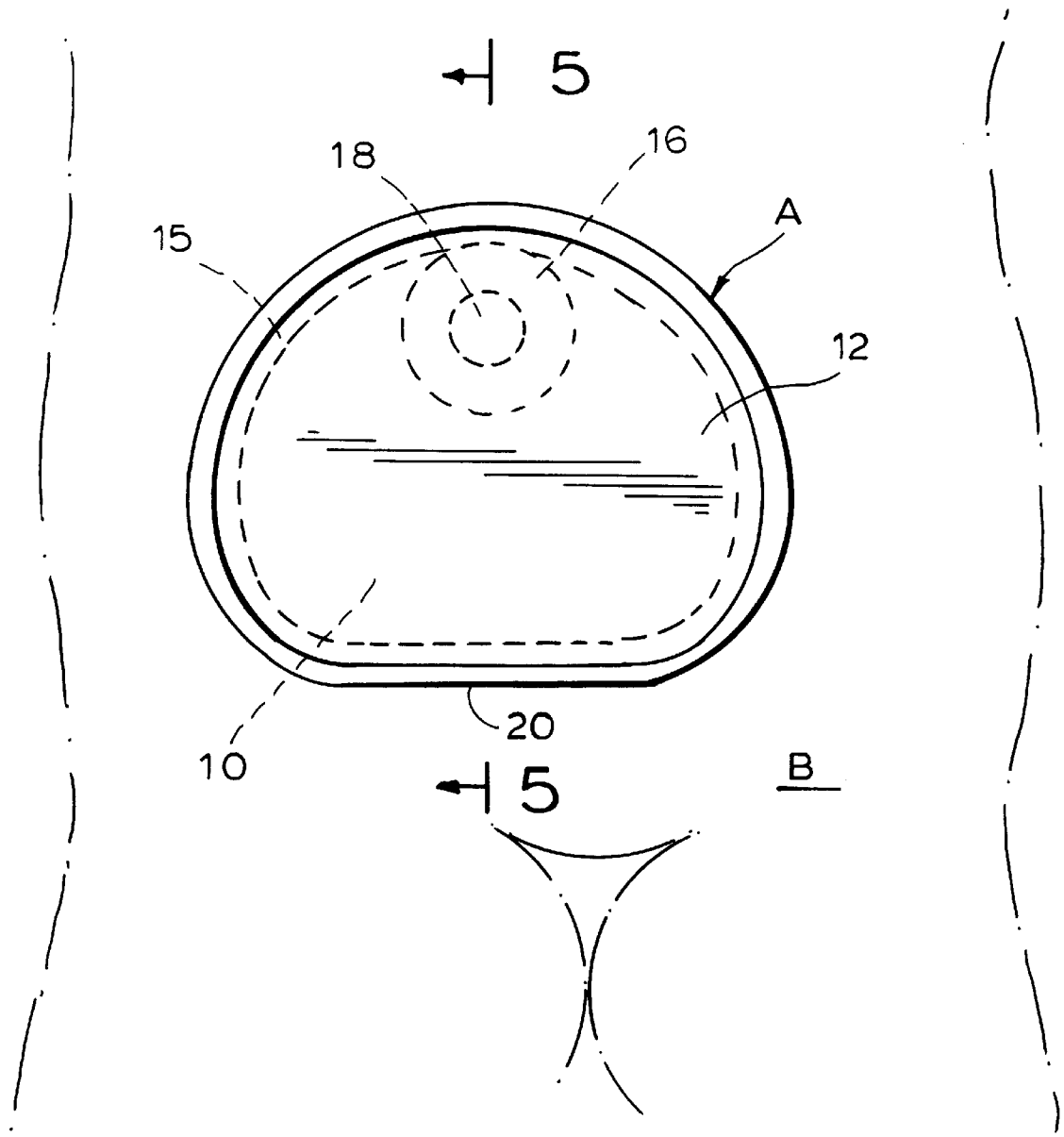
F I G. 4

SELF-SUPPORTING OSTOMY POUCH

This is a continuation of application Ser. No. 08/445,609, filed May 22, 1995 now abandoned.

BACKGROUND OF THE INVENTION

The present invention relates to ostomy devices of the type which include a receptacle or pouch for waste collection and more particularly to such a pouch which is adapted to adhere directly to the body and thus be self-supporting and which is shaped to more closely follow the contours of the body for increased comfort.

Certain surgical procedures known as colostomy, ileostomy and urostomy result in an opening in the abdominal wall, called a stoma, which permits waste discharge from the interior of a body cavity. Since the patient has no control over the waste discharge, it is often necessary for the patients who have undergone these surgical procedures to utilize an ostomy device to protect the stoma and collect the waste material as it is discharged.

Over the years, ostomy devices of a variety of different types and constructions have been utilized. Various materials and adhesives have been developed to increase the utility and wearability of same.

The conventional device includes a waste collection receptacle or pouch connected to an adhesive coated faceplate which serves to affix the pouch to the body. The pouch includes first and second thin film walls which are sealed by heat welding along the periphery to form the contour of the pouch. The faceplate is provided with skin friendly adhesive to seal the pouch to the skin surrounding the stoma. The faceplate and pouch have aligned openings which are adapted to receive the stoma.

However, because the pouch is much larger than the faceplate and is connected to the faceplate only along a ring weld surrounding the stoma receiving opening, in the pouch, the pouch tends to dangle from the body, like a pocket. When mounted in this way, the entire weight of the pouch is felt at the junction site with the body, in the area of the stoma, creating an unpleasant sensation.

My invention overcomes this disadvantage by having the pouch wall itself adhere directly to the body, over a substantial area of the wall surface. This eliminates the dangling of the pouch and more evenly distributes the weight.

In addition, conventional pouches are shaped without any consideration of the contours of the body. They are normally mounted in a position where the major axis of the pouch is parallel to the vertical axis of the body. In my invention, the configuration of the pouch is designed to better follow the contours of the body, resulting in a more comfortable fit.

SUMMARY OF THE INVENTION

It is, therefore, a prime object of the present invention to provide an ostomy pouch which is self-supporting such that it does not dangle and is hence the weight of the pouch is more evenly distributed over a larger area of the body.

It is another object of the present invention to provide an ostomy pouch which is form fitted to the contours of the body and hence is more comfortable to wear.

In accordance with one aspect of the present invention, an ostomy device is provided including waste collection pouch having a wall adapated to be situated adajacent the body. An adhesive layer is situated on the pouch wall is adapted to affix the pouch wall directly to the body.

In one preferred emodiment, the adhesive layer covers substantially the entire surface of the wall. In a second preferred embodiment, the adhesive layer covers a section of the surface of the wall along the periphery of the pouch.

The pouch may be substantially oval in configuration, with the major axis adapted to extend laterally. The bottom edge of the pouch may include a substantially linear section. Alternately, the bottom edge of the pouch may include a substantially inwardly indented section.

The pouch may be substantially circular in configuration. In this case, the bottom edge of the pouch may include a substantially linear section or an inwardly indented section, as well.

An adhesive backed collar may be provided. The collar is affixed to the wall surrounding the stoma receiving inlet.

In accordance with another aspect of the present invention, an ostomy device is provided including a waste collection pouch having a wall adapted to be situated adjacent the body. Means are provided for adhesively affixing the pouch to the body. The pouch is substantially oval in configuration and is adapted to be affixed to the body with its major axis extending laterally.

The pouch may have a bottom edge with a substantially linear section. Alternatively, the bottom edge may have a substantially inwardly indented section.

In accordance with another aspect of the present invention, an ostomy device is provided including waste collection pouch having a wall. Means are provided for adhesively affixing the pouch to the body. The pouch is substantially circular in configuration.

The pouch may have a bottom edge with a subtantially linear section. Alternately, the bottom edge may have a substantially inwardly indented section.

To these and the such other objects which may hereinafter appear, the present invention relates to a self-supporting ostomy pouch, as described in the following specification, set forth in the annexed claims and illustrated in the accompanying drawings, wherein like numerals refer to like parts, and in which:

BRIEF DESCRIPTION OF DRAWINGS

FIG. 4 is a plan view of another form of the first preferred embodiment of the present invention, as it appears when affixed to the body;

DETAILED DESCRIPTION OF THE DRAWINGS

As seen in the figures, the ostomy device of the present invention comprises a pouch, generally designed A, which is formed of two sheets of thin, flexible film. The film sheets form the pouch walls 10 and 12. The film is preferrably fabricated from materials which possess the properties of being moisture impermeable, odor impermeable and are capable of being heat sealed or impulse welded. Suitable materials include polyethylene, copolymers of polyethylene and ethylene vinyl acetate, copolymers of polyethylene acetate, copolymers of vinyl chloride and polyvinylidene chloride and laminates thereof. The pouch walls are preferably from about 2 to 4 mils thick. The walls are sealed around their periphery to provide a waste receptacle or pouch. The end of the pouch may be closed or open, as desired.

Figure 5:
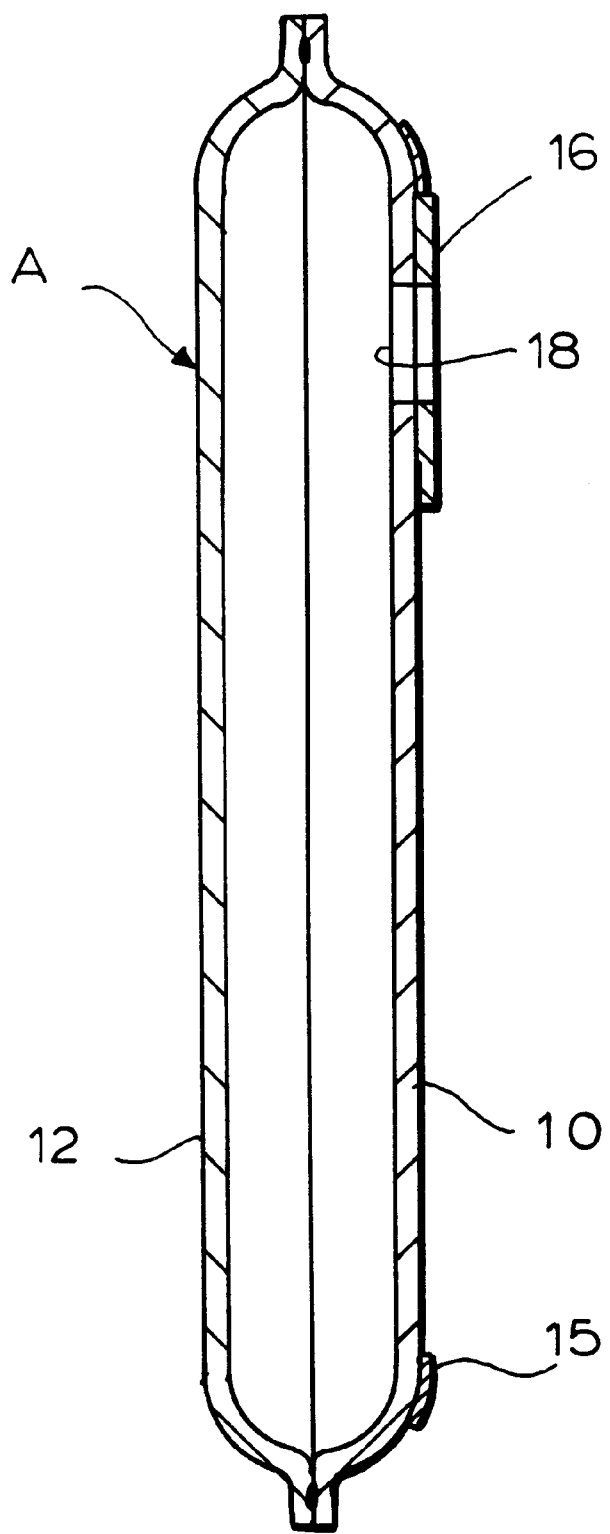
FIG. 5 is a side cross-sectional view taken along line 5—5 of FIG. 4.

Wall 10, which is designed to be situated adjacent the body, generally designed B, may have a skin-friendly surface texture. This surface is provided with a layer of adhesive so that it may be affixed directly to the skin. This adhesive layer may cover the entire surface of wall 10, as shown by layer 14 illustrated in FIGS. 1, 3, 6 and 7, or may be a layer 15 which is situated in a section located periphery of the pouch, as along the periphery, illustrated in FIGS. 4 and 5. In either case, a substantial portion of the surface of wall 10 is covered with the adhesive so that the pouch does not dangle or flop but instead the entire wall is retained adjacent to the body, more evenly distributing the weight of the pouch over a greater area of the body.

The adhesive layer on pouch wall 10 may be composed of any pressure sensitive adhesive suitable for use on human skin and capable of supporting the weight of the appliance. Preferably, the adhesive consists of an elastomeric substance such as polyisobutylene containing one or more hydrocolloids as taught by Chen in U.S. Pat. No. 3,339,546, by Chen et al. in U.S. Pat. No. 4,192,785, by Pawelchak in U.S. Pat. No. 4,393,080. This layer can additionally include a styrene type block copolymer as taught by Doyle et al. in U.S. Pat. No. 4,551,490. The adhesive layer will be from about 20 to about 70 mils thick.

For additional support and enhanced sealing of the skin surrounding the stoma, a microporous collar 16 may be provided. Collar 16 is welded or otherwise affixed to pouch wall 10, surrounding the stoma receiving inlet opening 18. Preferably, the weld will be in the shape of a ring concentric with opening 18.

Collar 18 consists of a pressure sensitive adhesive layer cast onto a backing. The adhesive layer is preferably 4 mils thick. The adhesive layer can be an acrylic microporous adhesive as taught by Copeland in U.S. Pat. No. 3,121,021, a microporous hydrocolloid adhesive as taught by Cilento in U.S. Pat. No. 4,427,727, or a polyisobutylene-hydrocolloid containing adhesive as taught by Chen in U.S. Pat. No. 3,339,546, by Chen et al. in U.S. Pat. No. 4,192,785, by Pawelchak in U.S. Pat. No. 4,393,080, or it can be adhesive composition containing a styrene type block copolymer in addition to the polyisobutylene and hydrocolloids as taught by Doyle et al. in U.S. Pat. No. 4,551,490.

The backing may include a non-woven polyethylene material. An EVA/polyethylene perforated film, approximately 2 mils thick, may be bonded to one surface of the non-woven material. The adhesive layer is cast over the film. The other surface of the non-woven material is welded to pouch wall 10.

Figure 1:
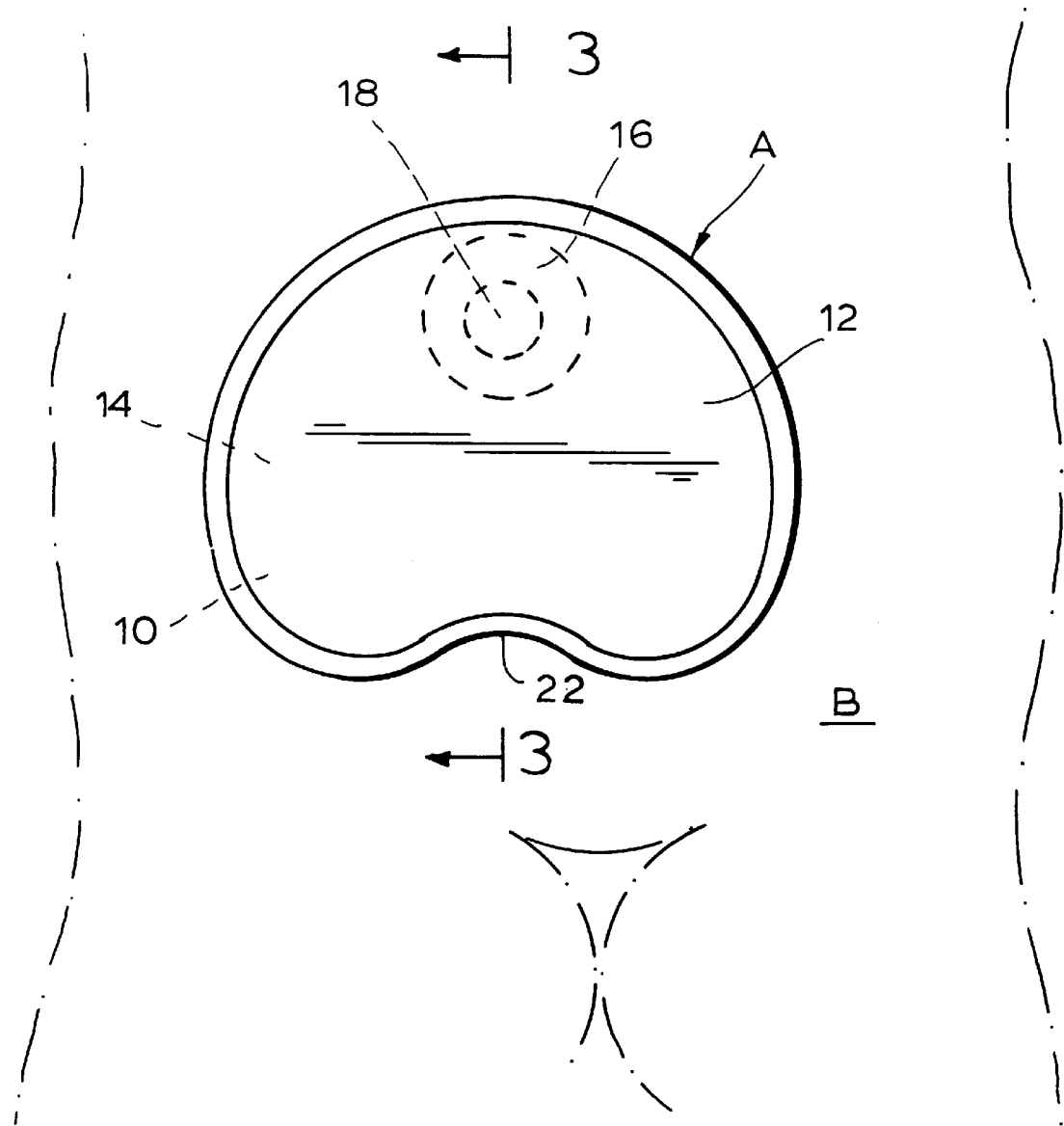
FIG. 1 is a plan view of a first preferred embodiment of the pouch of the present invention, as it appears when affixed to the body.
Figure 2:
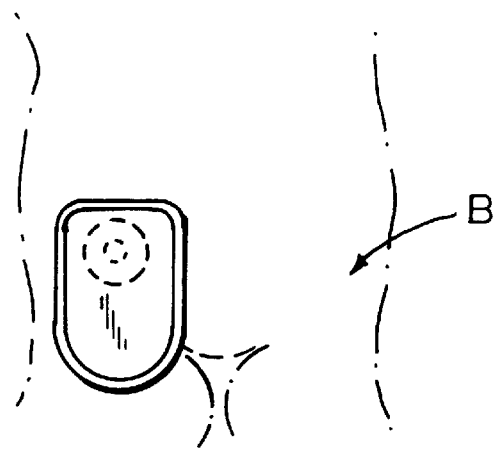
FIG. 2 is a view of a conventional one piece ostomy device, as it appears when affixed to the body.

The shape of the pouch is different from that of the conventional pouch, as illustrated in FIG. 2. The conventional pouch tends to be elongated in a direction parallel to the axis of the body B, a shape which does not take into account the contours of the body of the wearer.

Figure 6:
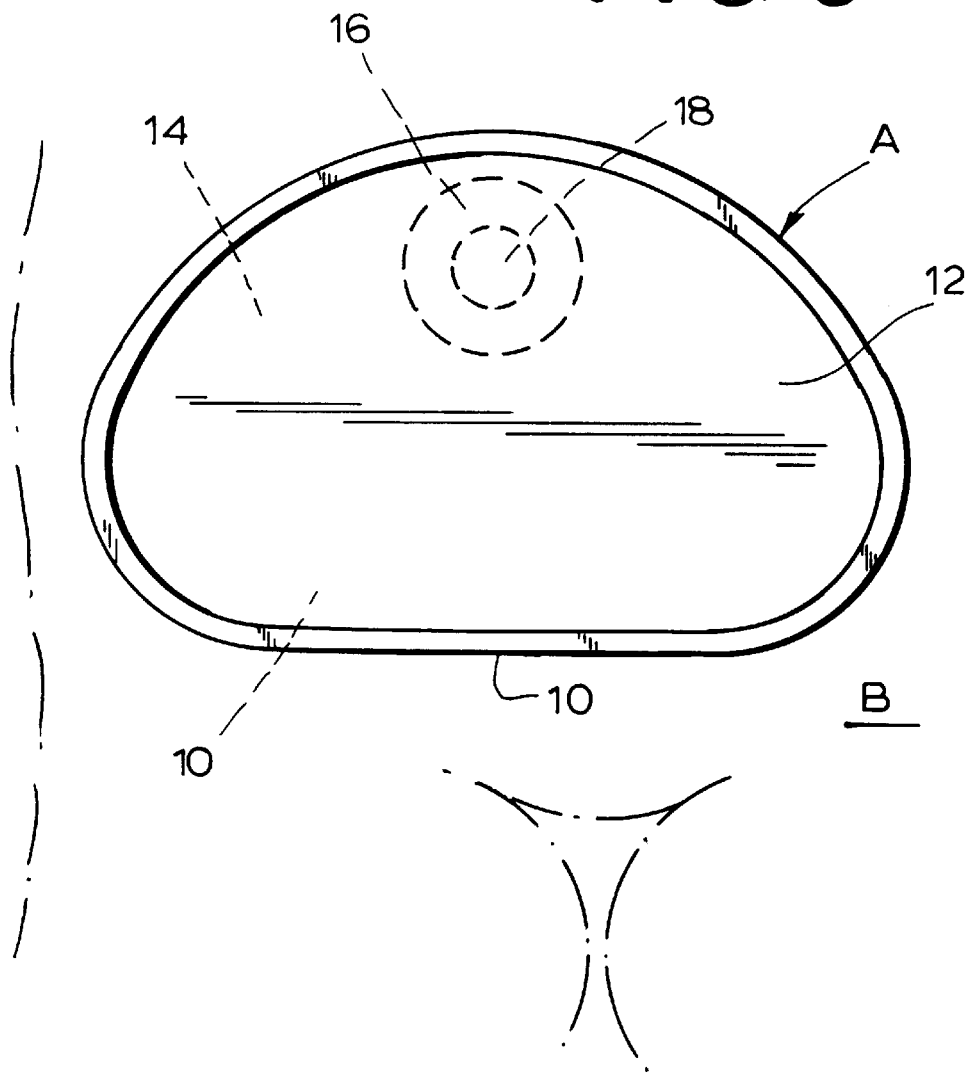
FIG. 6 is a plan view of a second preferred embodiment of the present invention, as it appears when affixed to the body.
Figure 3:
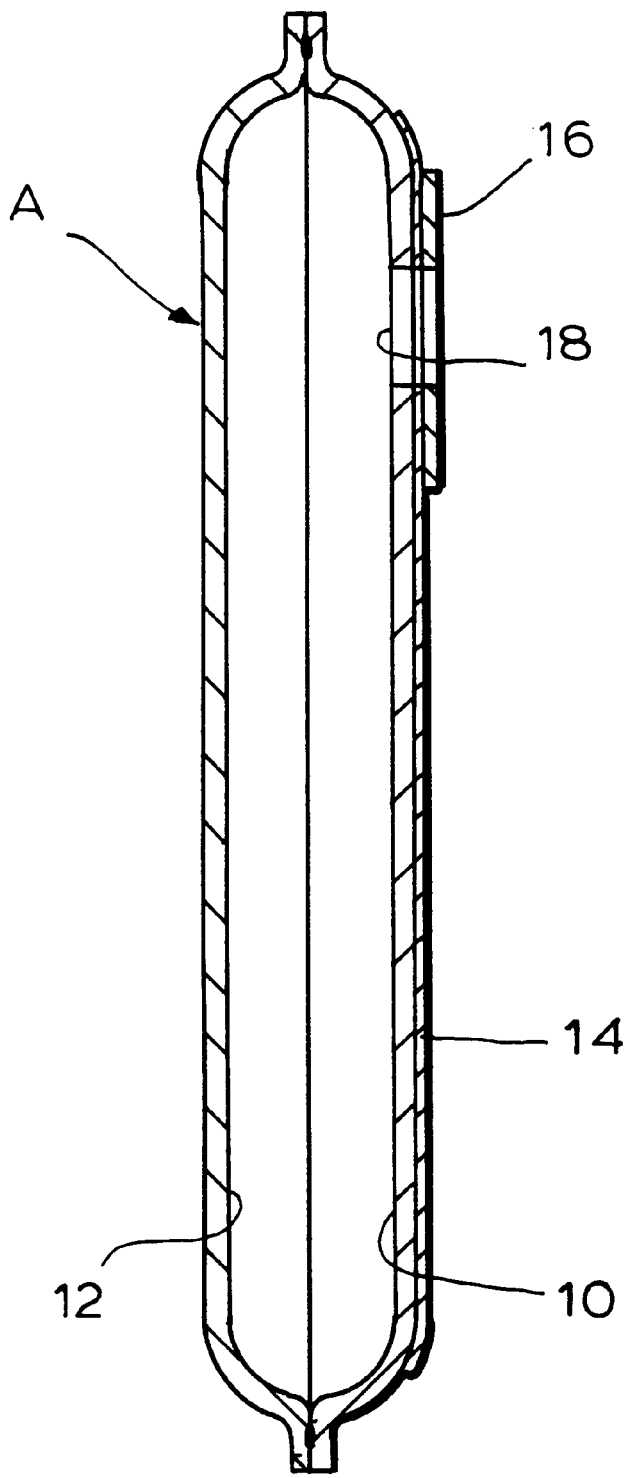
FIG. 3 is a side cross-sectional view taken along line 3—3 of FIG. 1.
Figure 7:
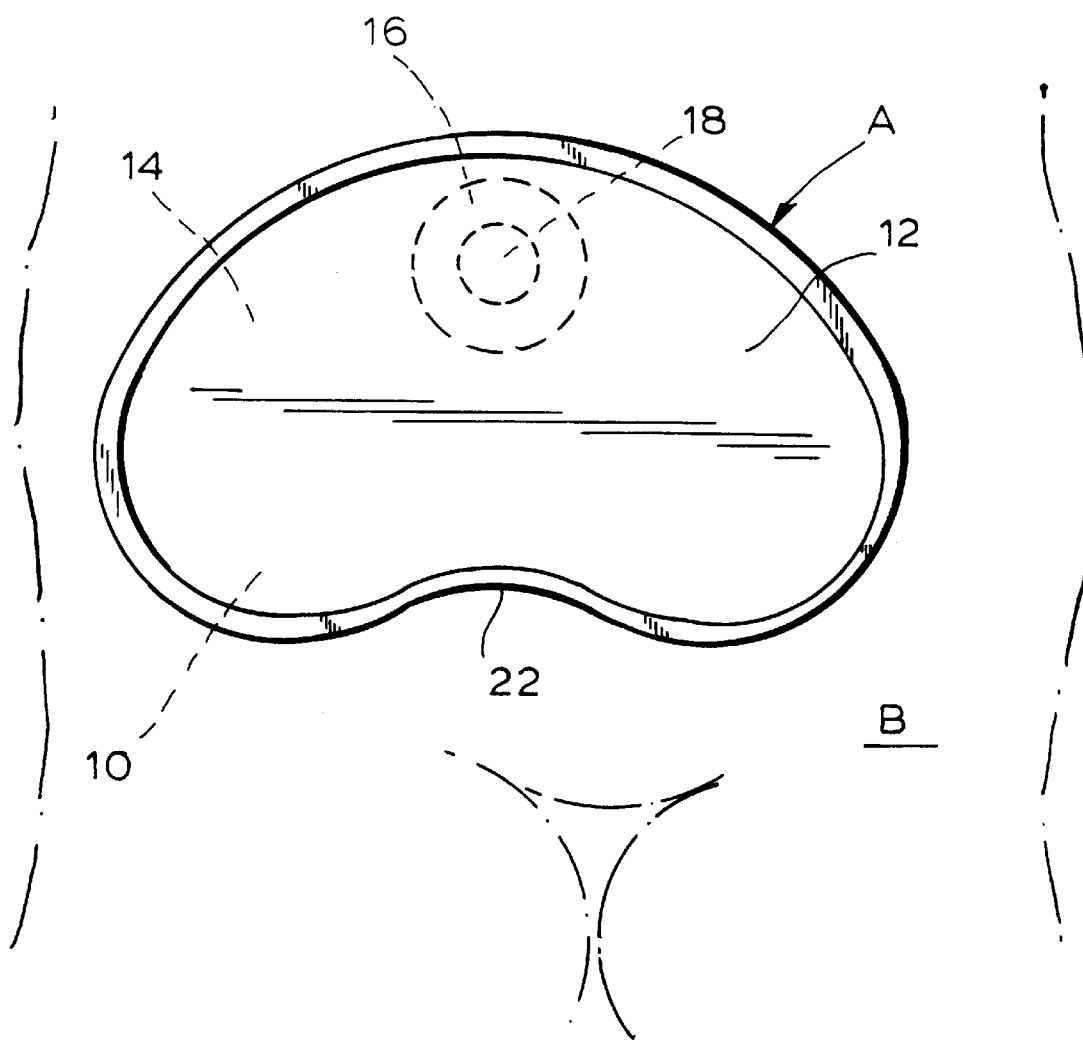
FIG. 7 is a plan view of another form of the second preferred embodiment of the present invention, as it appears when affixed to the body.

My pouch, on the other hand, is either substantially oval in shape, as seen in FIGS. 6 and 7, or substantially circular in shape, as shown in FIGS. 3 and 4. Whether oval or circular, the bottom edge may have a linear section 20 or an inwardly indented section 22. When oval, the pouch is adapted to be affixed to the body with its longer or major axis extending laterally.

It will now be appreciated that the present invention relates to an ostomy device with a waste collection pouch having a wall and an adhesive layer on the wall so as to affix the wall directly to the body. Mounting the pouch in this way eliminates dangling and more evenly distributes the weight. Moreover, the pouch is shaped to follow the contours of the body for a more comfortable fit.

While only a limited number of preferred embodiments have been disclosed for purposes of illustration, it is obvious that many variations and modifications could be made thereto. It is intended to cover all of these variations and modifications which fall within the scope of the present invention, as defined by the following claims.

I claim:

1. An ostomy device for attachment to a patient's body comprising a waste collection pouch having an inner wall and an outer wall, said inner wall having a stomal opening for receiving waste from the patient's body therethrough, each of said walls having a periphery, said inner and outer walls being joined to each other near said peripheries, said inner wall having a first adhesive layer of contactable biocompatible adhesive about said periphery of said inner wall, said first adhesive layer being capable of adhesively attaching said inner wall directly to the patient's body when in contact therewith, said stomal opening being defined by an inner wall border, and sealing means on said border for sealing said border to the patient's body.

2. The ostomy device of claim 1 wherein said first adhesive layer covers substantially an entire surface of said inner wall.

3. The ostomy device of claim 1 wherein said pouch is substantially oval in configuration and is adapted to be affixed to the patient's body with its major axis extending laterally.

4. The ostomy device of claim 1 wherein said pouch is substantially circular in configuration.

5. The ostomy device of claim 1 wherein said pouch has a bottom edge and wherein said bottom edge comprises a substantially linear section.

6. The ostomy device of claim 1 wherein said pouch has a bottom edge and wherein said bottom edge comprises a substantially inwardly indented section.

7. The ostomy device of claim 1 wherein said first adhesive layer comprises a hydrocolloid adhesive.

8. The ostomy device of claim 1 wherein said sealing means comprises a collar affixed to said inner wall border of said stomal opening, said collar having a second adhesive layer for sealing said border to the patient's body.

9. The ostomy device of claim 8 wherein said second adhesive layer includes a hydrocolloid adhesive.

10. The ostomy device of claim 1 wherein said sealing means is a biocompatible adhesive.

* * * * *